United States Patent [19]

Dunn et al.

[11] Patent Number: 4,531,519

[45] Date of Patent: Jul. 30, 1985

[54] VASCULAR CLAMP

[76] Inventors: David C. Dunn, 11 Trumpington Rd., Cambridge, CB2 2AJ; David Scarrow, 6 Monmouth Paddock, North St. Philip, Somerset, both of England

[21] Appl. No.: 621,881

[22] Filed: Jun. 18, 1984

Related U.S. Application Data

[63] Continuation of Ser. No. 512,021, Jul. 8, 1983, abandoned, which is a continuation of Ser. No. 311,390, Oct. 10, 1981, , which is a continuation of Ser. No. 159,632, Jun. 16, 1980, abandoned.

[30] Foreign Application Priority Data

Jun. 21, 1979 [GB] United Kingdom ................ 7921630

[51] Int. Cl.$^3$ ............................................. A61B 17/12
[52] U.S. Cl. .................................... 128/327; 128/325; 128/326; 128/346
[58] Field of Search ............... 128/327, 346, 325, 686, 128/DIG. 20, DIG. 25

[56] References Cited

U.S. PATENT DOCUMENTS

| 1,810,027 | 6/1931 | Moran et al. | 128/327 X |
| 2,161,393 | 6/1939 | Tye | 128/327 |
| 2,511,269 | 6/1950 | Jones | 128/327 |
| 2,533,924 | 12/1950 | Foley | 128/327 X |
| 3,257,694 | 6/1966 | Litwin | 24/16 |
| 3,538,917 | 11/1970 | Selker | 128/326 |
| 3,730,186 | 5/1973 | Edmunds | 128/325 |
| 3,993,076 | 11/1976 | Fogarty | 128/325 |

FOREIGN PATENT DOCUMENTS 1268034 3/1972 United Kingdom ............... 128/327

Primary Examiner—Michael H. Thaler

[57] ABSTRACT

A vascular clamp for use in surgery has a body in the form of a tapering flexible envelope, with an inlet tube at the broader end. An external strip at the broader end provides a slot through which the tail of the envelope can be threaded after passing it around the vessel. The envelope is then inflated, e.g. by a syringe, to compress the vessel. A tap closes the inlet tube after inflation, and can be operated to partially deflate the envelope and so check for leaks of blood. The disclosure also includes a method of using the vascular clamp for occluding a blood vessel.

8 Claims, 2 Drawing Figures

VASCULAR CLAMP

This application is a continuation of application Ser. No. 512,021 filed July 8, 1983, now abandoned which is a continuation of Ser. No. 311,390 filed Oct. 10, 1981, which is a continuation of Ser. No. 159,632 filed June 16, 1980, now abandoned.

This invention relates to devices, and a method of using same for clamping blood vessels or the like biological vessels having flexible walls.

U.K. Patent Specification No. 1268034 describes a vascular clamp comprising an elongate hollow body of which at least one wall is flexible and which is or can be curved to embrace e.g. a blood vessel with said flexible wall on the inside of the curve, and an inlet tube at one end of the body for inflation of the body thereby to clamp the vessel embraced by the body. The body is typically made of flexible plastics material, and has a filament extending from one end of the body to be threaded behind the vessel to be clamped and then used to draw the body behind the vessel. A retaining ring is provided through which the filament can be threaded and which embraces and retains the ends of the body in the curved configuration. The present invention relates to certain improvements in this type of vascular clamp.

In one aspect of the invention the elongate hollow body of the vascular clamp takes the form of a flat envelope of flexible fluid-impermeable sheet material which tapers from one end portion to the other, and has a strip of material extending transversely across the envelope at the broader end region and secured to the edges of the envelope to provide a slot between itself and the envelope through which the narrower end portion of the envelope can be threaded. A transverse seal may be provided across the envelope intermediate its ends so that the narrower end portion is not inflated in use.

The long taper to the flat envelope considerably facilitates the manipulation of the envelope in passing it around the vessel, and the transverse strip provides a more satisfactory method of retaining the tail portion of the envelope than a separate retaining ring as used hitherto and cannot become detached and left in the body cavity.

In another aspect of the invention the inlet tube to the inflatable envelope is provided with a tap to shut off the flow of fluid when the envelope is inflated and which can be subsequently temporarily opened to allow partial deflation of the envelope, so that for example some flow of blood can take place to check for any leakage at the site of the operation.

In order that the invention may be more clearly understood, and readily carried into effect, a preferred embodiment, given by way of example only, will now be described with reference to the accompanying drawings, wherein.

Figure 1:
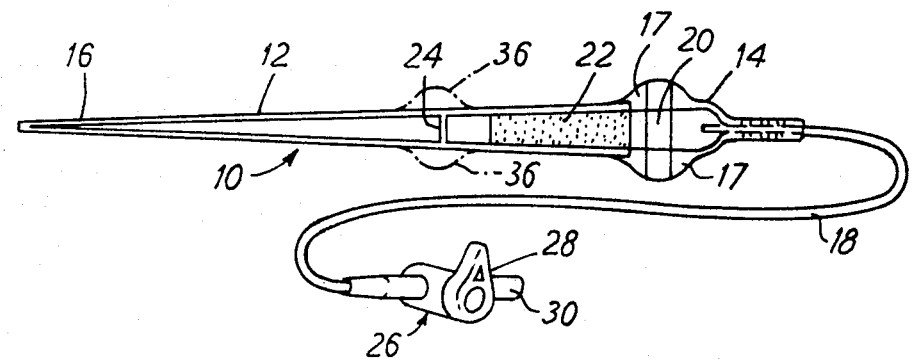
FIG. 1 shows the vascular clamp prior to use.

Referring to the drawings, and firstly to FIG. 1; the vascular clamp comprises a body 10 made from two layers of flexible plastics film sealed together at 12 around their edges. The body tapers from a broad end 14 to a narrow end 16, with a pair of flaps 17 near the broad end, and a flexible plastics inflation tube 18 is sealed into the broad end. A strip 20 of flexible plastics sheet material extends transversely across one face of the body at the broad end portion in the region of the flaps 17, and is welded to the flaps at its ends. A layer of plastics foam material 22 is secured at the same face of the body adjacent the strip 20. A transverse seal 24 extends across the body on the side of the foam layer 22 remote from the strip 20. The outer end of the inflation tube 18 is connected to a tap 26 having a manually rotatable arrow shaped valve member 28 within a cylindrical tap body. The valve member has a through passage which is transverse to the inflation tube 18 when the arrow head of the valve member is similarly disposed, as in FIG. 1, and is aligned with the inflation tube when the arrow head of the valve member is so disposed as in FIG. 2. The tap is provided with a spigot 30 for connection thereto of a nozzle of a syringe 32.

Figure 2:
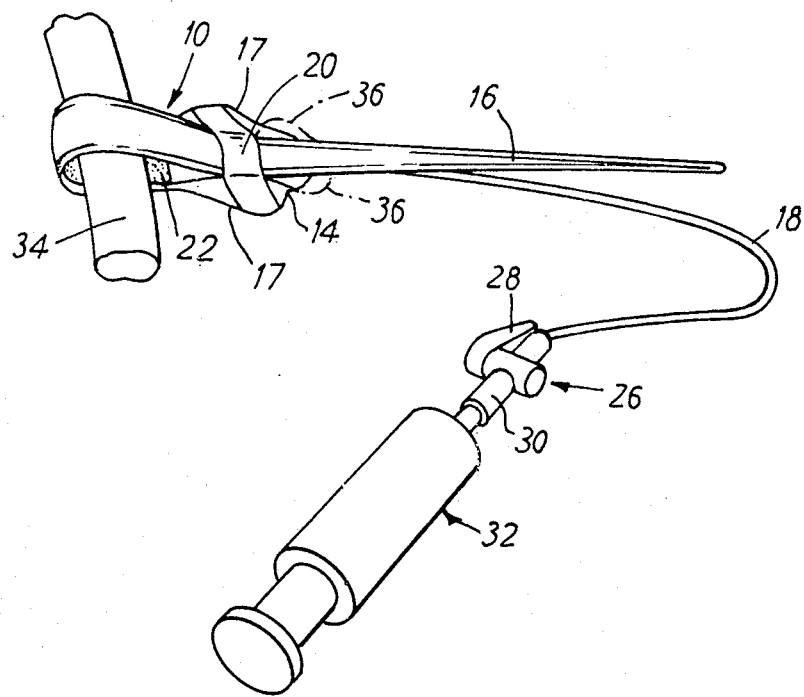
FIG. 2 shows a perspective view of the vascular clamp in use.

In use, the tail portion 16 of the body is threaded under the vessel 34 (for example a blood vessel of a patient) to be occluded, and is then taken around the vessel and threaded through the slot between the strip 20 and the body, as shown in FIG. 2. The vessel seats in the region of the body occupied by the foam layer 22. Then, with the tap 26 open and a syringe 32 connected to it, fluid is injected by means of the syringe along the tube 18 to inflate the portion of the body between the transverse seal 24 and the tube 18; i.e. the portion of the body embracing the vessel 34. This causes the vessel to be occluded. The layer of film material of the body remote from the strip 20 is preferably thicker than the layer adjacent the strip, so that on inflation the envelope tends to expand more inwardly towards the vessel. The tap 26 is then closed to retain the inflating fluid (which may for example be air, water or other gas or liquid). Subsequently, the tap can be temporarily opened to release some of the inflating fluid, and thereby allow a limited flow of biological fluid through the vessel. This can be useful to check for any leaks of biological fluid in the region of the operation being performed on the patient. When the clamp is no longer required, the tap is fully opened to allow the body to deflate, and the narrow end portion is released from the strip 20 and the clamp is withdrawn.

The body 10 may be formed with an additional pair of flaps 36, suitably in the region of the transverse seal 2. These flaps 36 can be folded over the body when threading the tail portion under the strip 20, and then released so as to provide, as seen in FIG. 2, lateral abutments resisting accidental withdrawal of the tail portion.

Instead of the marginal seals 12 being broader in the region of the flaps 17 and the flaps 36 (if present), the relatively narrow marginal seal 12 could be continued in these regions, so that the internal width of the inflatable portion increases in these regions. This has the effect of increasing the inflation in these regions and more securely holding the device in its operative condition.

A radio-opaque material may be incorporated in the device, for example as a stripe in the inlet tube 18, so that it can be detected by X-ray photography if inadvertently left in the body cavity.

I claim:

1. A vascular clamp for occluding a single blood vessel or the like during surgery, comprising a flat elongated envelope of flexible fluid-impermeable sheet material which can be curved to embrace said blood vessel intended to be occluded by said vascular clamp, the envelope tapering from a narrow end towards a broader end with a fluid inlet tube at the broader end for inflation of the envelope to occlude said vessel embraced by said envelope, and having a strip of material extending transversely across the envelope at the broader end region and secured to the edges of the envelope to provide a slot between itself and the envelope through which the narrower end portion of the envelope can be threaded, a transverse seal being provided across the envelope intermediate its ends so that the narrower end portion is not inflated in use, the length of the uninflatable portion being greater than the length of the inflatable portion, and a region of foam material between said strip and said transverse seal and on the same side of the envelope as said strip, the envelope being formed with a distal lateral enlargement in the region of the transverse seal which enlargement can be deflected to allow the narrower end portion, including the distal enlargement to be threaded through said slot and which resiliently resumes its laterally projecting configuration when released, the envelope being formed from two superimposed layers of plastics film material peripherally sealed together, the peripheral seal between the layers following the outline of the distal enlargement so that the internal width of the envelope is locally wider in this region, the transverse seal being located within the distal enlargement.

2. A vascular clamp according to claim 1 wherein the envelope is also formed with a proximal lateral enlargement in the region of the transverse strip, the peripheral seal between the layers following the outline of the proximal enlargement so that the internal width of the envelope is locally wider in this region, the transverse strip being welded at its ends to the envelope coincidentally with the peripheral seal.

3. A vascular clamp according to claim 2 wherein each lateral enlargement is provided by a gradual increase in the overall width of the envelope.

4. A vascular clamp for occluding blood vessels or the like during surgery, comprising a flat elongated envelope of flexible fluid-impermeable sheet material which tapers from a narrow end towards a broader end with a fluid inlet tube at the broader end for inflating the envelope, and having a strip of material extending transversely across the envelope at the broader end region and secured to the edges of the envelope to provide a slot between itself and the envelope through which the narrower end portion of the envelope can be threaded, a transverse seal being provided across the envelope intermediate its ends so that the narrower end portion is not inflated in use, the length of the uninflatable portion being greater than the length of the inflatable portion, the envelope being formed with a proximal lateral enlargement in the region of said transverse strip the envelope being formed from two superimposed layers of plastics film material peripherally sealed together, the peripheral seal between the layers following the outline of said proximal enlargement so that the internal width of the envelope is locally wider in the region, the transverse strip being welded at its ends to the envelope conicidentally with the peripheral seal.

5. A vascular clamp for occluding a single blood vessel or the like during surgery, comprising a flat elongated envelope of flexible fluid-impermeable sheet material which can be curved to embrace said blood vessel intended to be occluded by said vascular clamp, the envelope tapering from a narrow end towards a broader end with a fluid inlet tube at the broader end for inflation of the envelope to occlude said vessel embraced by said envelope, and having a strip of material extending transversely across the envelope at the broader end region and secured to the edges of the envelope to provide a slot between itself and the envelope through which the narrower end portion of the envelope can be threaded, a transverse seal being provided across the envelope intermediate its ends so that the narrower end portion is not inflated in use, the length of the uninflatable portion being greater than the length of the inflatable portion, said fluid inlet tube entering the broader end of the envelope in a direction substantially lengthwise of the envelope, the envelope being formed with a distal lateral enlargement in the region of the transverse seal, which enlargement can be deflected to allow the narrower end portion, including the distal enlargement, to be threaded through said slot and which resiliently resumes its laterally projecting configuration when released, the envelope being formed from two superimposed layers of plastics film material peripherally sealed together, the peripheral seal between the layers following the outline of the distal enlargement so that the internal width of the envelope is locally wider in this region, the transverse seal being located within the distal enlargement.

6. A vascular clamp according to claim 5 wherein the envelope is also formed with a proximal lateral enlargement in the region of the transverse strip, the peripheral seal between the layers following the outline of the proximal englargement so that the internal width of the envelope is locally wider in this region, the transverse strip beng welded at its ends to the envelope coincidentally with the peripheral seal.

7. A vascular clamp for occluding a single blood vessel or the like during surgery, comprising a flat elongated envelope of flexible fluid-impermeable sheet material which can be curved to embrace said blood vessel intended to be occluded by said vascular clamp, the envelope tapering from a narrow end towards a broader end with a fluid inlet tube at the broader end for inflation of the envelope to occlude said vessel embraced by said envelope, and having a strip of material extending transversely across the envelope at the broader end region and secured to the edges of the envelope to provide a slot between itself and the envelope through which the narrower end of the envelope can be threaded, a transverse seal being provided across the envelope intermediate its ends so that the narrower end portion is not inflated in use, the length of the uninflatable portion being greater than the length of the inflatable portion, said fluid inlet tube entering the broader end of the envelope in a direction substantially lengthwise of the envelope, the envelope being provided with a proximal lateral enlargement in the region of said transverse strip and a distal lateral enlargement in the region of the transverse seal, the envelope being formed from two superimposed layers of plastics film material peripherally sealed together, the peripheral seal between the layers following the outline of the distal engagement so that the internal width of the envelope is locally wider in this region, the transverse seal being welded at its ends to the envelope coincidentally with the peripheral seal.

8. A vascular clamp for occluding a single blood vessel or the like during surgery, comprising a flat elongated envelope of flexible fluid-impermeable sheet material which can be curved to embrace said blood vessel intended to be occluded by said vascular clamp, the envelope tapering from a narrow end towards a broader end with a fluid inlet tube at the broader end for inflation of the envelope, and having a strip of material extending transversely across the envelope at the broader end region and secured to the edges of the envelope to provide a slot between itself and the envelope through which the narrower end portion of the envelope can be threaded, a transverse seal being provided across the envelope intermediate its ends so that the narrower end portion is not inflated in use, the length of the uninflatable portion being greater than the length of the inflatable portion, the envelope being formed from two superimposed layers of plastics film material peripherally sealed together and being provided with a lateral enlargement in the region of said transverse strip, the strip being welded at its ends to the envelope coincidentally with the peripheral seal within the region of the lateral enlargement, which enlargement can be deflected to allow the narrower end portion, including the distal enlargement, to be threaded through said slot and which resiliently resumes its laterally projecting configuration when released, the peripheral seal between the layers following the outline of the distal enlargement so that the internal width of the envelope is locally wider in this region, the transverse seal being located within the distal enlargement.

* * * * *